United States Patent [19]

Wang

[11] Patent Number: 5,120,307

[45] Date of Patent: Jun. 9, 1992

[54] METHOD FOR INJECTING VISCOUS FLUID INTO THE EYE TO LIFE RETINAL MEMBRANE

[75] Inventor: Carl C. T. Wang, Piedmont, Calif.

[73] Assignee: Alcon Laboratories, Inc., Fort Worth, Tex.

[21] Appl. No.: 572,320

[22] Filed: Aug. 22, 1990

Related U.S. Application Data

[63] Continuation of Ser. No. 209,503, Jun. 21, 1988, abandoned.

[51] Int. Cl.$^5$ ............................................. A61M 31/00
[52] U.S. Cl. .................................................. 604/51
[58] Field of Search ................ 606/107; 604/19, 22, 604/27, 28, 30, 35, 51, 118, 120, 131, 140, 141, 143, 146, 151, 246, 264, 283, 294, 295; 128/DIG. 1, 912; 433/95

[56] References Cited

U.S. PATENT DOCUMENTS

| | | | |
|---|---|---|---|
| 1,046,166 | 12/1912 | Flaherty . | |
| 1,105,275 | 7/1914 | Ingalls . | |
| 2,017,276 | 10/1935 | Ericson et al. | 604/143 |
| 2,484,657 | 10/1949 | Son . | |
| 2,865,371 | 12/1958 | Dorbecker et al. . | |
| 3,589,363 | 6/1971 | Banko et al. | 604/22 |
| 3,768,472 | 9/1973 | Hodosh et al. | 604/143 |
| 3,812,855 | 5/1974 | Banko . | |
| 3,884,237 | 5/1975 | O'Malley et al. | 128/303.14 |
| 4,041,947 | 8/1977 | Weiss et al. | 604/22 |
| 4,177,810 | 12/1979 | Gourlandt | 604/144 |
| 4,274,411 | 6/1981 | Dotson, Jr. . | |
| 4,328,803 | 5/1982 | Pape | 604/28 |
| 4,331,130 | 5/1982 | Lewicky | 604/21 |
| 4,340,037 | 7/1982 | Lewicky | 604/49 |
| 4,351,335 | 9/1982 | Whitney et al. | 604/143 |
| 4,424,055 | 1/1984 | Herman . | |
| 4,508,532 | 4/1985 | Drews et al. | 604/22 |
| 4,670,006 | 6/1987 | Sinnett et al. . | |
| 4,678,459 | 7/1987 | Onik et al. | 604/22 |
| 4,705,500 | 11/1987 | Reimels et al. | 604/22 |
| 4,713,446 | 12/1987 | DeVore et al. . | |
| 4,717,384 | 1/1988 | Waldeisen | 604/143 |
| 4,764,165 | 8/1988 | Reimels et al. | 604/22 |
| 4,768,506 | 9/1988 | Parker et al. . | |
| 4,820,264 | 4/1989 | Matsui et al. | 604/294 |

FOREIGN PATENT DOCUMENTS

| | | | |
|---|---|---|---|
| 253057 | 7/1964 | Australia . | |
| 273404 | 12/1964 | Australia . | |
| 60320 | 3/1971 | Australia . | |
| 0151519 | 8/1985 | European Pat. Off. | 604/283 |
| 0232458 | 8/1987 | European Pat. Off. . | |
| 2907832 | 10/1980 | Fed. Rep. of Germany | 604/283 |
| WO80/01310 | 6/1980 | PCT Int'l Appl. . | |
| 8602257 | 4/1986 | PCT Int'l Appl. | 604/22 |
| 8706455 | 11/1987 | PCT Int'l Appl. | 604/51 |
| 988285 | 12/1981 | U.S.S.R. . | |
| 1364333 | 7/1988 | U.S.S.R. . | |
| 0016647 | 7/1911 | United Kingdom | 604/141 |

OTHER PUBLICATIONS

EFD, 1000X1 Operating Instructions.
Healon brochure, Pharmacia.

*Primary Examiner*—John D. Yasko
*Assistant Examiner*—Anthony M. Gutowski
*Attorney, Agent, or Firm*—Ronald C. Fish

[57] ABSTRACT

A method for injecting viscous material into the eye. In the injection into the eye, sufficient material is injected to separate a membrane from the retina so that intraocular scissors may be manipulated between the membrane and the retina to cut the attachment points. The membrane is then aspirated away. The injection is done using a standard glue injector with a one-shot and a continuous mode. The glue injector is pneumatically coupled through a sterile filter and a custom adaptor to a sterile syringe storing the material to be injected.

7 Claims, 7 Drawing Sheets

METHOD FOR INJECTING VISCOUS FLUID INTO THE EYE TO LIFE RETINAL MEMBRANE

This application is a continuation of application Ser. No. 07/209,503, filed June 21, 1988, now abandoned.

BACKGROUND OF THE INVENTION

The invention pertains to the field of intraocular surgery, and, more particularly, to surgical procedures for removal of pre-retinal or post-retinal membranes.

It is a frequent post-operative complication following surgical procedures in the posterior region of the eye that a glia cell membrane will form and attach itself to the retina. Anytime the choroid layer is stimulated such as by cutting, laser burning, lesion caused by probing or cryo or thermal damage, or any other form of stimulation, fibro and glia cells will be pumped from the choroid by pneumatic processes. Glia cells are glue-like and serve to repair damage surrounding the lesion formed by the stimulation. This excretion of glia cells is often used to "glue" a detached retina to the choroid. Unfortunately, the body's control mechanisms of secretion of fibro and glia cells are not finely tuned enough to stop secretion of the cells at the precise time when enough cells have been excreted to do the job. Excretion of excess cells often results in formation of a membrane of cells over the retina between the retina and the lens of the eye resulting in obstruction of the light path to the retina. Sometimes, in the case of detached retinas, the membrane forms between the retina and the choroid.

The formation of these membranes is called proliferative disease. This disease frequently is a post-operative complication of surgical procedures for reattachment of detached retinas. One of the negative effects that results from this phenomenon is that the glia cells initially form a single cell layer membrane over the retina or between the retina and the choroid. This membrane is attached to the retina at various points by what are sometimes referred to as "nails". The retina is normally attached to the choroid by a structure which is similar to VELCRO TM brand hook and loop fabric.

There is a problem of spontaneous detachment of the retina if proliferative disease develops. This can occur for the following reason. The membranes initially form as a single cell layer. Later, the cells often rearrange themselves into a multiple cell layer without growing further. Attachments to the retina at the locations of the "nails" may be quite strong. Because the same number of cells that were formerly a single cell layer have become a multiple cell thickness layer, the membrane tends to shrink. This shrinkage causes stresses on the retina at the positions of the "nails" which can result in holes being pulled in the retina or in spontaneous detachment of the retina from the choroid.

Another problem of membrane formation is that in the prior art process for removing such membranes, forces can be applied to the retina by the tools used or through the "nail" connection points to damage the retina structure. Typically, this happens by pulling a hole in the retina at the position of a nail or by punching a hole in the retina through mistakes in manipulation of the tools used. Also, the process of removing a post-retinal membrane, i.e., one between the retina and the choroid, can result in cutting off circulation of blood to the rods and cones of the retina. To understand these problems further, consider the following.

In the prior art, surgeons have removed these membranes from the retina using several techniques. One such technique is to take a vertical intraocular scissors with the blades closed and insert the tip of the scissors between the membrane and the retina. This is a very delicate process and requires great manual dexterity since the space between the membrane and the retina is not large. After the scissors are inserted, the blades are very gently opened to separate the membrane from the retina. This process is continued until the location of a "nail" is encountered. Then a horizontal intraocular scissor is inserted in the space between the cell membrane and the retina in such a manner as to cut the "nail". This process is repeated until the "nails" have been found and severed or pulled loose. After the cell membrane has been separated in this manner from the retina, it is usually removed using a vitrectomy probe.

Another prior art technique is to use an instrument which has a fiber-optic probe with a hook. The hook is very small and is formed of the tip of the light pipe. The hook is used by inserting its tip between the membrane and the retina and separating the membrane from the retina by pulling gently on the membrane.

The difficulty with both of these prior art approaches is that damage to the retina can easily result. One type of damage can result if the mechanical forces applied to the membrane and transmitted to the retina at the locations of the "nail" are too large. This can result in holes being pulled in the retina at the position of the "nails". Further, detachment of the retina from the choroid can also result if the force exerted on the retina through the nails exceeds the force holding the retina to the choroid. Another type of damage that can result is through inadvertent movement of the instrument while the retina is engaged on the hook which results in excessive force being applied to the retina. If the tools are not manipulated with great skill, holes can be poked in the retina. These holes result from the relatively concentrated forces acting on the retina at the tips of the instruments. Even a slight misapplication of force can result in this type of damage to the retina.

Accordingly, a need has arisen for a system which can be used to gently separate the membranes from the retina without causing spontaneous detachment of the retina and without pulling or punching holes in the retina thereby allowing the "nails" to be cut without damage to the retina.

SUMMARY OF THE INVENTION

According to the teachings of the invention, an apparatus and method is taught for injecting a viscous fluid in the space between the membrane and the retina. This viscous fluid forms pockets in the space between the membrane and the retina all around the "nail" attachments. These pockets of viscous fluid apply diffuse pressure to the membrane and retina to separate these structures. Separation of the membrane from the retina allows horizontally oriented intraocular scissors to be worked into the space between the membrane and the retina through the viscous fluid. These scissors may be worked to the position of the "nails" which may then be cut thereby separating the membrane from the retina. Sometimes the process of injecting the viscous material alone will pull the nails loose. This process may be done without endangering the retina because the pressure applied to the retina is very diffuse and is not localized in one small area thereby creating stresses in that area which exceed the strength of the retina.

In the preferred embodiment, a viscous fluid with self-adhering properties is used for injection. Several brands of fluid have been found to be adequate for purposes of practicing the invention. One such candidate is HEALON brand sodium hyaluronate marketed by Pharmacia. Another fluid which is acceptable for purposes of practicing the invention is AMVISC brand sodium hyaluronate marketed by Johnson and Johnson.

The fluid is injected using a modified glue injection device which is commercially available. In a preferred embodiment, a model 1000×L glue injector manufactured by EFD of East Providence, R.I. is used. This glue injector is coupled to a source of pressurized air and has a pressure regulator. The device also generates its own vacuum using a venturi and the pressurized air. The glue injector also has a foot switch and a pressurized air output which is connected to a syringe in which the viscous fluid is stored. The amount of pneumatic pressure at the pressurized air output is controlled by manipulation of a control on the front panel of the unit which controls the internal pressure regulator. The pressure may be set at anywhere between zero and 40 pounds per square inch.

The device has two modes. The first mode is the continuous mode, and the second mode is the "one shot" mode. In the first mode, when the foot switch is depressed, pressurized air builds up to the pressure set by the pressure regulator and continues at that level for as long as the foot switch is pressed. When the foot switch is released, the output pneumatic tube is either vented to atmosphere or vacuum is applied to it to prevent "woozing" of fluid out of the needle of the syringe connected to the pneumatic output. The level of vacuum which is applied during this stage is controlled by another control on the front panel of the unit. In the second mode, a pressure pulse having a duration which is variable is applied to the pneumatic output tube. This pulse starts when the foot switch is pressed, and ends when the predetermined interval has passed. The duration of the pulse is set by a timer control which can be manipulated from the front panel of the unit. The standard glue injection syringe of the system is replaced by a sterile HEALON brand sodium hyaluronate or other viscous fluid injection syringe onto which the pneumatic output tube from the pressure regulation unit is connected. A special sealing adaptor comprising a threaded bezel ring mated with a threaded adaptor having an O ring is used to form a mechanical bond between the syringe and the pneumatic output tube and to form a pneumatic seal. The bezel ring fits around the syringe and engages a flange thereof. A plunger or piston inside the injection syringe is in pneumatic communication with the pressure regulation unit through the special adaptor just described and the pneumatic hose. This allows pneumatic pressure applied by the pressure regulation unit to be coupled to the piston to force it to move downward in the syringe. This forces viscous fluid stored in the syringe from the tip of a hollow needle which is affixed to the cylinder of the syringe. A filter is placed in the pneumatic line between the pressure regulating unit and the syringe. This filter filters out all foreign bodies having dimensions greater than a particular size from the pneumatic air flow to the syringe.

A method of using the above described apparatus for performing a surgical procedure to remove either a pre or post-retinal membrane is as follows. The syringe is attached to the pressure regulating unit. The pressure regulating unit is located outside the sterile field, and the attachment of the sterile syringe is made to the pneumatic tube end after it has been placed in the sterile field. The desired pneumatic pressure is than set by manipulation of the appropriate front panel control. This is done regardless of whether the continuous or one-shot mode is selected. Next, the one-shot or continuous mode is selected by manipulation of the appropriate switch on the front panel of the pressure regulation unit. In the one-shot mode, the desired pulse duration is set by manipulating the appropriate control on the front panel. Then the vacuum level which will be applied to the pneumatic output tube upon completion of the pneumatic pressure pulse is set by manipulation of the appropriate control on the front panel of the pressure regulation unit. In the continuous mode, both the pressure and vacuum level are set in a similar fashion. Pressure and vacuum levels for either mode are set using experimental injections outside the eye and inside the sterile field so as to obtain the desired injection rate for the then existing conditions of temperature and health, i.e., strength, of the retina. The surgeon will have already made an assessment of the strength of the retina from previous surgery.

Next, the tip of the needle is placed in the space between the retina and the pre or post-retinal membrane. Thereafter, the foot switch is depressed to cause injection of the HEALON brand sodium hyaluronate into the space between the pre or post-retinal membrane and the retina. This causes the pre or post-retinal membrane to "inflate" as it is pushed away from the retina by the injection of the viscous fluid. The surgeon exercises judgement to stop the injection when it looks like too much stress is being applied to the retina through a nail attachment. This injection process is repeated at a sufficient number of locations to either break and/or isolate all the "nails" or connection points between the pre or post-retinal membrane and the retina itself. The "nails" which have not been broken by the injection process itself are then cut using horizontally oriented intraocular scissors.

Once all the connection points have been severed, the membrane is usually removed using a vitrectomy probe or other aspiration device. The HEALON brand sodium hyaluronate or other viscous material remaining in the eye is then removed using a vitrectomy probe or other aspiration device.

DETAILED DESCRIPTION OF THE PREFERRED EMBODIMENT

Figure 1:
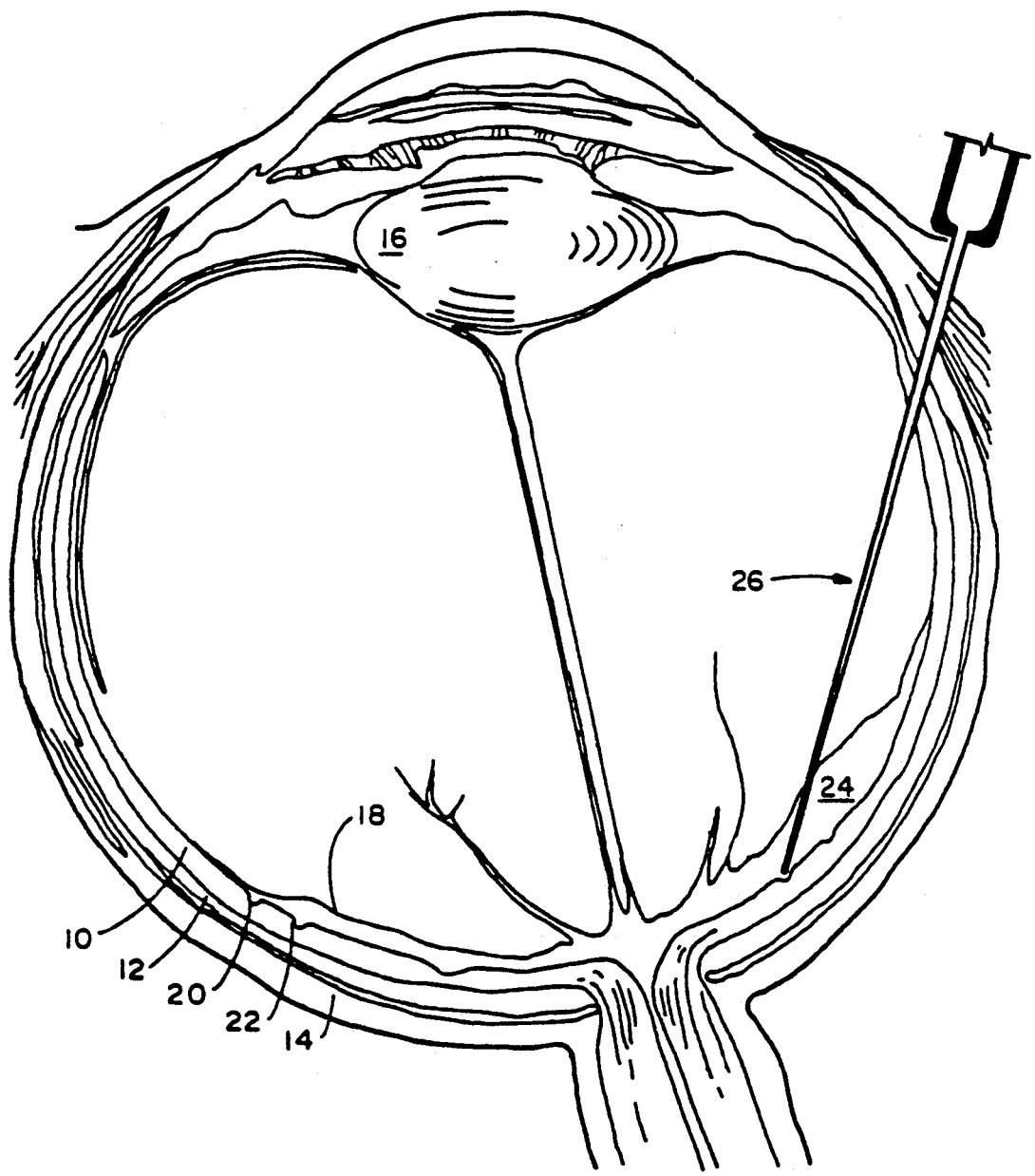
FIG. 1 is an anatomical sketch of the eye illustrating the relationship between the retina and the choroid and showing the manner of injection of fluid between a pre-retinal membrane and the retina.

Referring to FIG. 1, there is shown in cross section an anatomical diagram of the eye. The particular portions of the eye of interest are the retina shown at 10 and the choroid shown at 12. Sometimes the retina becomes detached from the choroid for various reasons. When this happens, a medical procedure is performed to reattach the retina to the choroid. This is usually done by causing a lesion in the choroid by any one of several possible methods. Often laser energy is beamed through the sclera shown at 14 and through the choroid 12 to cause the lesion. Cutting, the application of heat or other mechanical stimulation may also be used to cause this lesion. The wound in the choroid causes growth of glia cells. These glia cells grow out from the lesion in the choroid and, because of their glue-like properties, they tend to reattach the retina to the choroid. However, because the body does not have sufficient control over the growth of these glia cells, they frequently form a single layer of cells in the form of a membrane between the retina and the lens 16. A portion of such a pre-retinal membrane is shown at 18. These pre-retinal membranes have a tendency to attach themselves to the retina at randomly spaced locations. Such attachment points or "nails" are shown symbolically at 20 and 22.

There are several difficulties that a preretinal membrane causes as a post-operative complication. First, the membrane obstructs light passage through the vitreous body to the retina thereby obstructing vision. Second, the pre-retinal membrane tends to rearrange itself from a one-cell layer membrane to a two-cell layer membrane. A segment of such a rearranged membrane is shown at 24. This latter phenomena causes difficulty because in the process of rearranging itself, the preretinal membrane shrinks thereby putting stress on the retina through the "nail" connections. This stress can wrinkle, tear, or detach the retina and is quite undesirable. A solution to this problem is to remove the preretinal membrane.

As noted above, the postoperative membrane is not always in a pre-retinal position. Sometimes it also forms between the retina and the choroid. Nevertheless, the same considerations apply since the post-retinal membrane also attaches itself to the retina sporadically at nail connection points and will rearrange itself from a single-cell layer to a multiple-cell layer thereby causing the problems noted above.

It has been found by the applicants that a good way to remove a membrane is to inject a viscous, selfadhering fluid such as HEALON brand gel between the membrane and the retina. This is done by inserting a needle into the interstices between the membrane and the retina and pumping the viscous gel into the interstices. FIG. 1 shows such a needle 26 in position to begin pumping fluid at 26.

Figure 2:
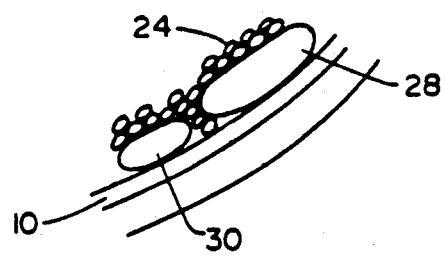
FIG. 2 is an illustration showing the structure of the eye and a pre-retinal membrane after injection of viscous fluid surrounding a nail attachment point.

Referring to FIG. 2, there is shown the result of injection of a viscous gel in the interstices between the membrane and the retina 10. The injection process forms bubbles of injected gel shown at 28 and 30. These bubbles lift the membrane 24 away from the retina 10 by applying diffuse pressure to both the retina and the membrane over a large area. This "large area" is relative to the stresses which are caused on the retina by tools used in the prior art. The prior art method of removing a membrane was using a mechanical hook to engage the membrane and lift it away from the retina. If the hook is not manipulated correctly, the tip of the hook impacts the retina in a small area. This causes localized forces which can raise the stress level in the retina above the levels that can be easily withstood by this delicate structure. The diffuse nature of the pressure applied by the injected gel according to the teachings of the invention tend to distribute the stress widely over the surface of the retina 10 and the membrane 24. Because the forces applied by the injected gel are spread out over a large area, the stress level at any particular point of the retina is less than the stress imposed in the retina in the prior art methods. The result of improper manipulation of the tools used in the prior art methods often was a torn retina or a retina with a hole punched therein. By eliminating the need to contact the retina with any hard instrument, the potential for damage to the retina is substantially reduced using the teachings of the invention.

Once injection of the gel is completed and the structure is as shown in FIG. 2 throughout the area covered by the membrane, the membrane may be detached. The membrane cannot simply be pulled off the retina using a hooked instrument since the nail attachments will tend to detach the retina from the choroid or tear a hole in the retina at the point of attachment. Therefore, it is necessary to cut the nail attachments with horizontally-oriented intraocular scissors. This is done by working the point of the intraocular scissors through the injected gel to the position of the nail and cutting the nail. This sequence of events is not depicted in FIG. 2, but those skilled in the art can appreciate how it is done.

Figure 3:
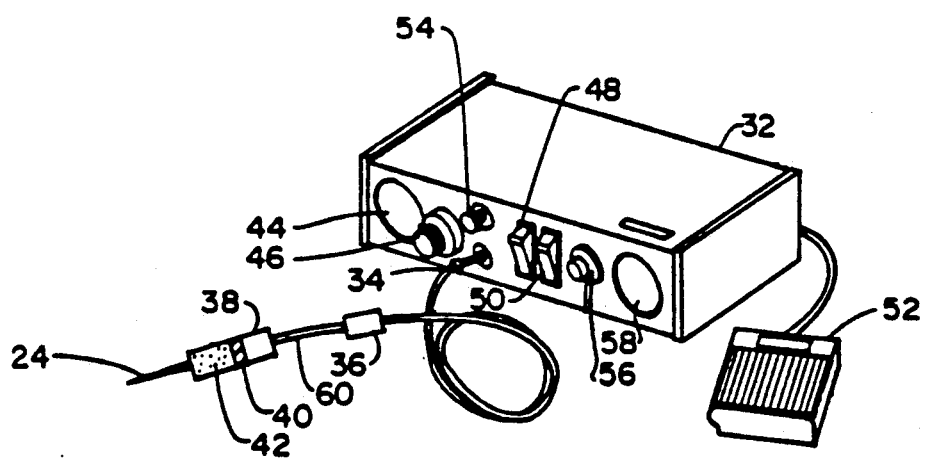
FIG. 3 is a diagram of the apparatus of the invention.

Referring to FIG. 3 there is shown a picture of a system which is adapted for injecting the gel 28 to lift the membrane away from the retina. The system is comprised of a pneumatic pressure and vacuum control unit 32 which will hereafter be referred to as the control unit. System unit 32 is an off-the-shelf glue injection controller manufactured by EFD of East Providence, R.I. Its model designation is 1000×L. The control unit 32 is coupled to an air pressure source by a connector (not shown) on the back side of the unit. In some embodiments, the control unit 32 may be coupled to a source of vacuum by a vacuum input (not shown) on the back side of the unit. The purpose of the control unit 32 is to regulate the amount of pneumatic pressure applied to a pneumatic output 34. This pneumatic output is coupled by a pneumatic hose 34a through an air filter 36 to a syringe 38. This syringe has a piston 40 therein which is driven by the pneumatic pressure toward an injection needle 26 thereby forcing any fluid stored in the cavity 42 of the syringe out from the tip of the injection needle 26. There are generally two types of syringes used for the same purpose. They differ in the type of flange that is attached to the syringe body. One type of syringe has two ears extending from opposite sides of the syringe barrel such as the syringe shown in FIG. 4. Another type of syringe has a polygon or round or nearly round shaped flange which surrounds the barrel. The two different types of syringe require different types of adapters for connection to the pneumatic hose.

The air filter 36 serves to filter any microscopic size particles from the flow of air in the pneumatic tubing 34. This air filter should either be sterile and disposable or autoclavable. The syringe 38, needle 26, and piston 40 also should be either autoclavable or sterile and disposable.

The control unit has an air pressure gauge 44 for monitoring the level of pneumatic pressure which is being applied to the syringe 38. The amount of pressure applied is controlled by an air pressure regulator inside the control unit which is controlled by a front panel knob 46. The control unit 32 has a power on/off switch 48, and a mode control switch 50. This mode control switch switches the control unit between a steady state mode and a "one-shot" mode. In the steady state mode, a level of pneumatic pressure set by manipulation of the air pressure regulator control knob 46 will be applied to the pneumatic output 34 beginning when a foot peddle control 52 is depressed and terminating when the foot peddle control 52 is released. In the "one-shot" mode, a pneumatic pulse is applied to the pneumatic output 34. The air pressure magnitude of this pulse is set by manipulation of the air pressure regulator control knob 46. The duration of this pneumatic pulse is controlled by manipulation of a time control knob 54. The pneumatic pulse is issued by the control unit 32 when the foot pedal 52 is depressed. The pneumatic pulse automatically terminates at the end of the interval set by the time control knob 54, regardless of when the foot pedal 52 is released.

For some low viscosity fluids it is advantageous to apply vacuum to the pneumatic output 34 at the end of the pneumatic pressure cycle. This vacuum pulls the piston 40 away from the needle 26, thereby aspirating fluid back into the needle 26. This prevents a last drop of fluid which may be clinging to the tip of the needle 26 from dripping from the needle tip at an inconvenient time or at some unintended location. The level of vacuum which is applied to the pneumatic output 34 is controlled by a vacuum control manipulation knob 56 on the front panel of the control unit. The level of vacuum may be adjusted with the aid of a vacuum pressure gauge 58. The level of vacuum set by the vacuum control knob 56 will automatically be applied at the end of every pneumatic pulse or application of pneumatic pressure to the output 34. If no vacuum aspiration is desired, the vacuum control knob 56 is manipulated so that zero vacuum pressure is indicated on the vacuum pressure gauge 58. Vacuum is generated in the control unit 32 by use of a venturi to convert pneumatic pressure of escaping air to subatmospheric pressure.

The pneumatic pressure on the output line 34 may be set anywhere from 1 to 100 psi. Typical operating pressures are on the order of 30-40 psi depending upon temperature and viscosity.

In operation, the control unit 32 is located outside the sterile field. A sterile pneumatic hose 34 is then unpackaged in this sterile field, and one end is connected to the pneumatic output. A sterile air filter 36 is then attached to the other end of the pneumatic hose 34 within the sterile field. A sterile prepackaged syringe containing the gel to be injected is then coupled to a segment of sterile pneumatic hose connected to the output of the air filter 36. In the preferred embodiment, the syringe 38 contains HEALON brand gel in cavity 42. More details on the structure of the syringe 38 and its adapter for coupling to the segment of pneumatic hose 60 will be given below.

Following attachment of the syringe to the pneumatic hose segment 60, the following procedure is used to perform the surgical procedure. First, the desired pneumatic peak pressure is set using the air pressure regulator control knob 46. It is desired to have a very small flow rate for injection of the gel to avoid applying sudden excess amounts of pressure to the retina and membrane. Therefore, the maximum pressure should be set no higher than 30-40 psi. The pressure is adjusted experimentally for the current conditions of viscosity and operating room temperature by placing the system in continuous or one-shot mode and depressing the foot pedal and observing the flow rate of gel emerging from the tip of the injection needle 26. If a higher flow rate is required, the air pressure regulator control knob 46 is manipulated to increase the pressure. If a lower flow rate is desired, a lower pneumatic pressure is set using the air pressure regulator control knob 46. The desired vacuum level, if any, is also set for the current conditions of viscosity and temperature.

Next, the appropriate mode is set. If the one-shot mode is selected, the time duration of the pneumatic pulse is set using time control knob 54. The foregoing steps for setting the desired injection rate are based upon not only the current conditions of temperature and viscosity, but also upon the health or strength of the retina. This latter information is generally available based upon previous surgery which caused the stimulation of the choroid which generated the membrane.

Next, the tip of the needle 26 is placed in the space between the retina and the membrane. Injection of fluid from the cavity 42 is then performed while the surgeon observes the inflation of the membrane. Injection is stopped if it looks like too much stress is being applied to the retina through a "nail" connection. This injection process is performed at a sufficient number of locations to thoroughly break off and/or isolate all the nail connection points between the membrane and the retina. Care is exercised to not pull holes in the retina at the positions of the nails or detach the retina from the choroid by applying excess force to the retina through the nails. The unbroken nails are then cut using horizontally oriented intraocular scissors. Finally, the membrane is removed through use of a vitrectomy probe or other aspiration instrument. The injected gel may then be removed with a vitrectomy probe or any other aspiration instrument.

Referring to FIGS. 4A and 4B, there is shown an exploded view of the injection syringe. The syringe is comprised of a main body 38 having a flange 62 and a syringe holder 64. The syringe holder 64 has a lock-in mechanism 66 which engages the flange 62. In the embodiment shown in FIGS. 4A and 4B, the flange 62 is engaged in the lock-in mechanism 66 in bayonet fashion, as shown generally at 68. The syringe body 38 has a piston 40 therein which is shown in phantom in FIG. 4A. This piston forms an air-tight and liquid-tight seal with the inside walls of the syringe body 38. The syringe body 38 terminates in an injection needle 26 (not shown) which is protected by a cover/handle 70. This cover/handle terminates in a projection 72 which can be threaded into the piston 40 for manual manipulation of the piston.

The syringe depicted in FIG. 4A is, with the exception of the syringe holder 64, a off-the-shelf HEALON storage syringe which is available from the manufacturer of HEALON brand gel. The syringe holder 64 is a specialized adapter which is constructed to allow the piston 40 to be manipulated by pneumatic pressure and vacuum in the input line 60. Thus, the cover 70 is only for purposes of protecting the injection needle 26 (not shown) and maintaining its sterility.

The syringe holder 64 engages the syringe body 38 to form a mechanical bond between the syringe body 38 and the pneumatic hose 60, as well as a pneumatic seal. To that end, the syringe holder 64 has an internal passageway 74 which is in fluid communication with the pneumatic tubing 60. When the syringe holder 64 engages the syringe body 38, an extension 76 of the syringe body on the syringe holder side of the flange 62 slides into the passageway 74 when the flange 62 is engaged in the lock-in mechanism 66. An O-ring seal (not shown) inside the passageway 74 engages the side walls of the section 76 of the syringe body to form the pneumatic seal.

Figure 5:
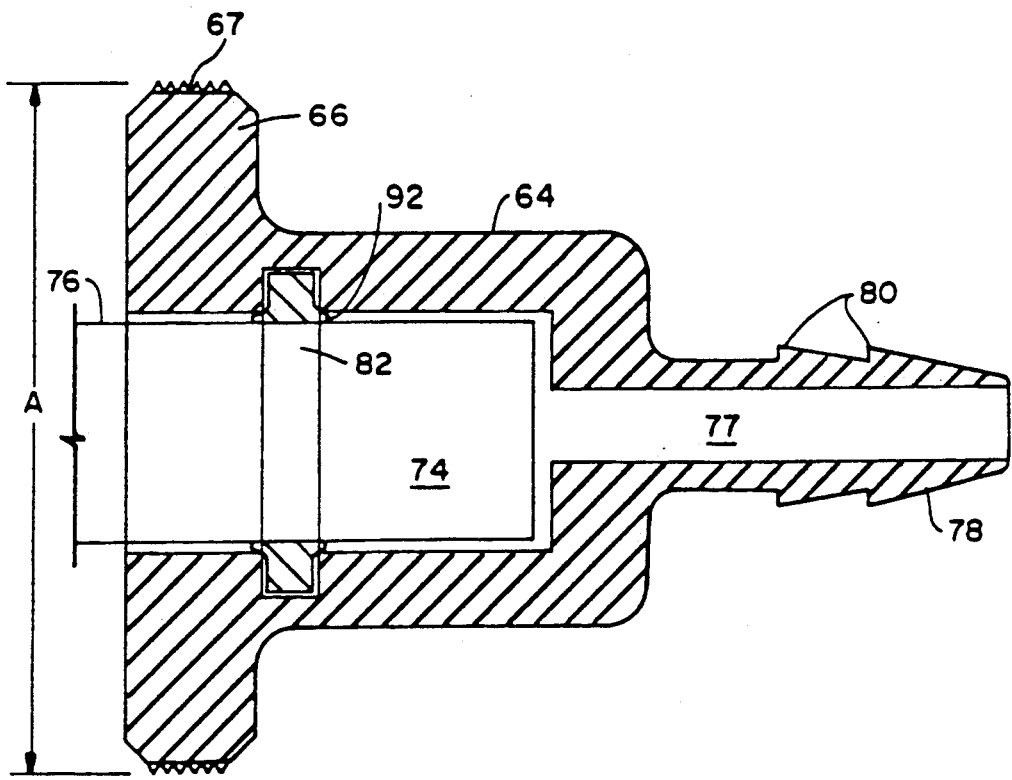
FIG. 5 is a cross-sectional view of a threaded adaptor for use with a threaded bezel ring for attaching the syringe to the pneumatic hose.

More details of the structure of the syringe holder 64 are illustrated in FIG. 5. The syringe holder is comprised of a main body 64 with a lock-in mechanism 66 formed thereon, typically by casting or injection molding. The main body has an internal passageway 74 which is in fluid communication with a second passageway 77 in a pneumatic-tube-engaging projection 78. This projection 78 has ribs 80 for engaging the flexible pneumatic tubing to form a mechanically sound connection and a pneumatic seal. The internal cavity 74 has a groove 82 formed therein in which an O-ring is placed. This O-ring should be of silicone or other flexible but autoclavable material.

Figure 6A:
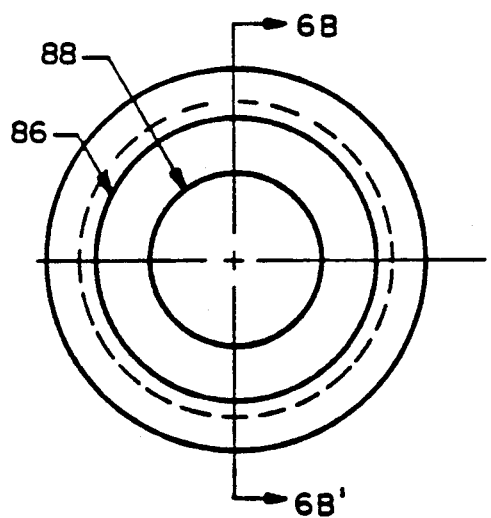
FIGS. 6A and 6B are end and cross-sectional views, respectively, of the threaded bezel ring for use with the threaded adapter of FIG. 5.
Figure 6B:
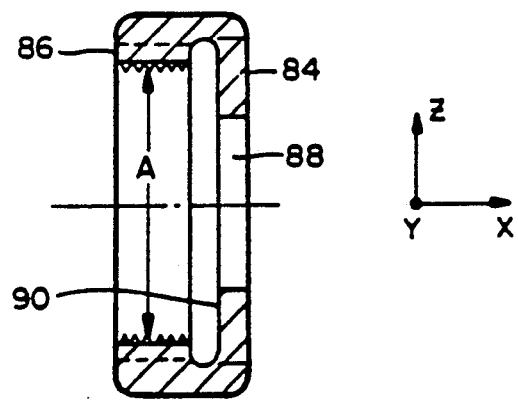

In the embodiment shown in FIG. 5, the outside edges of the lock-in mechanism 66 are threaded. These threads engage similar threads on the inside of a bezel ring 84 shown in FIGS. 6A and 6B. FIGS. 6A and 6B show a bezel ring for engaging the flange 62 in FIG. 4 as an alternative mechanism to the bayonet lock-in mechanism shown in FIG. 4. FIG. 6A is a plan view of this bezel ring, while FIG. 6B is a sectional view of the ring taken along the line 6B—6B' in FIG. 6A. The bezel ring is comprised of a main body 84 having a threaded portion 86 and an aperture 88. The aperture 88 slides over the main body 38 of the syringe in FIG. 4 until the flange 62 rests against the surface 90 shown in FIG. 6B. The portion 76 of the syringe main body extends through the aperture 88 in FIG. 6B into the main body 64 of the syringe holder. The inside diameter of the threaded portion 86, shown at A in FIG. 6B, matches the outside diameter of the lock-in portion 66 of the syringe holder 64. The lock-in portion 66 is then threaded into the threaded portion 86 of the bezel ring of FIG. 6B to form the mechanical union between the syringe holder 64 and the syringe body 38. The O-ring in the groove 82 then forms a pneumatic seal by engaging the walls of the portion 76 of the syringe body. This O-ring is shown at 92 in FIG. 5.

Figure 4:
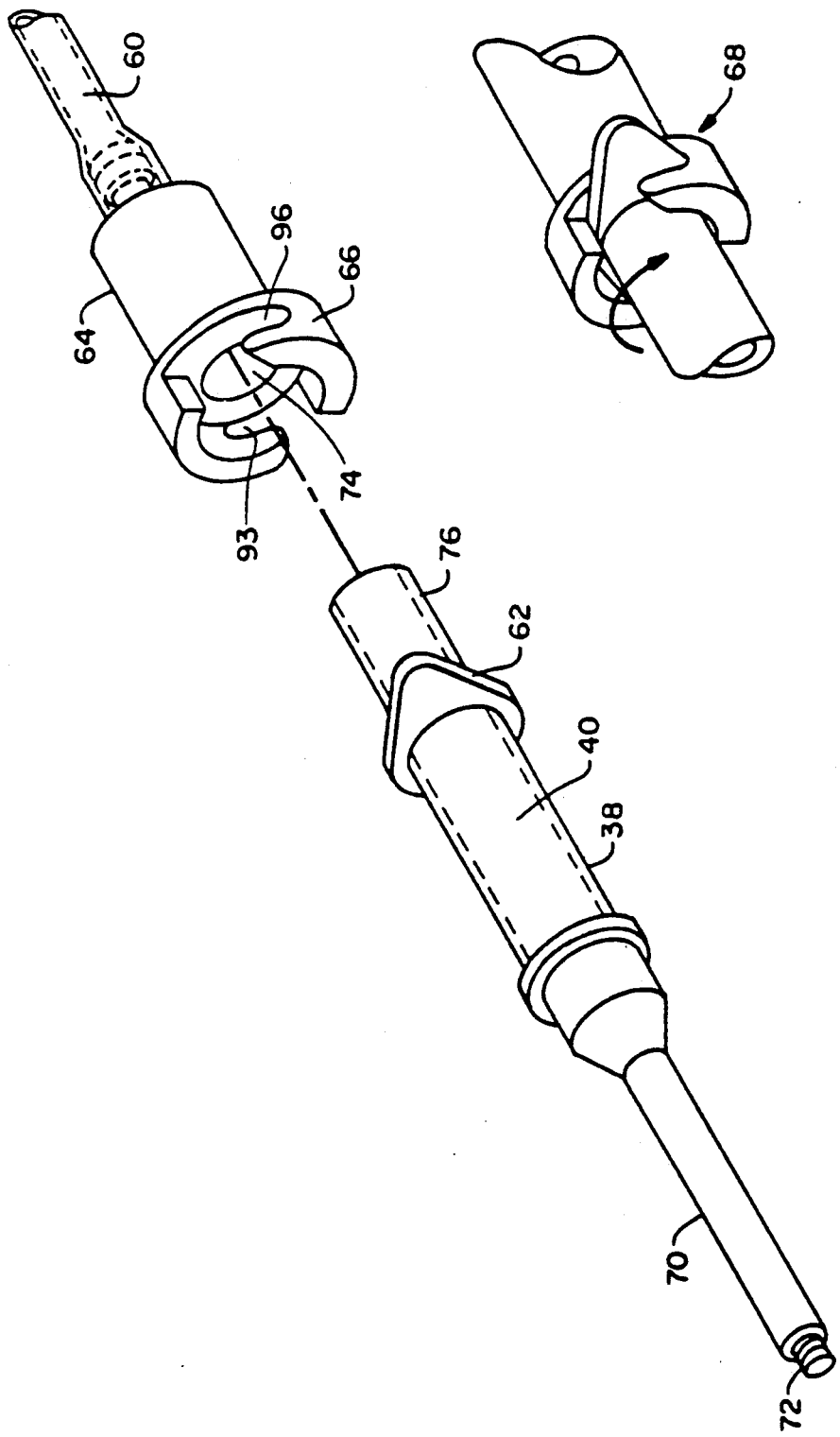
FIGS. 4A and 4B are exploded view of the injection syringe and the connection apparatus for connecting the syringe to the pneumatic hose.
Figure 7A:
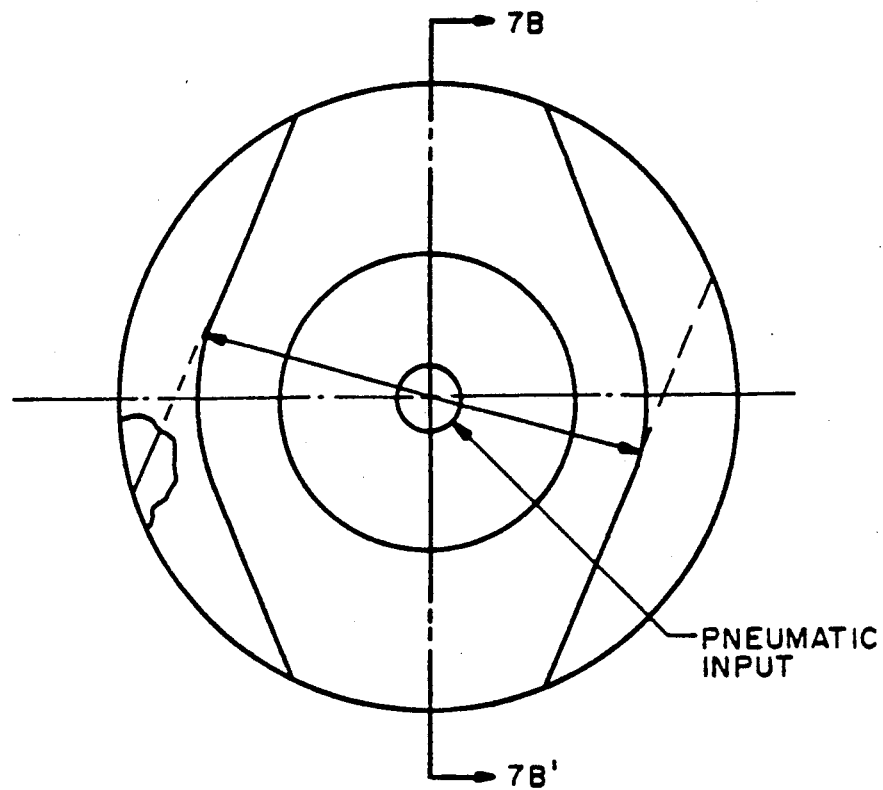
FIGS. 7A and 7B are end and cross-sectional views of a bayonet type connector for connecting the syringe to the pneumatic hose.
Figure 7B:
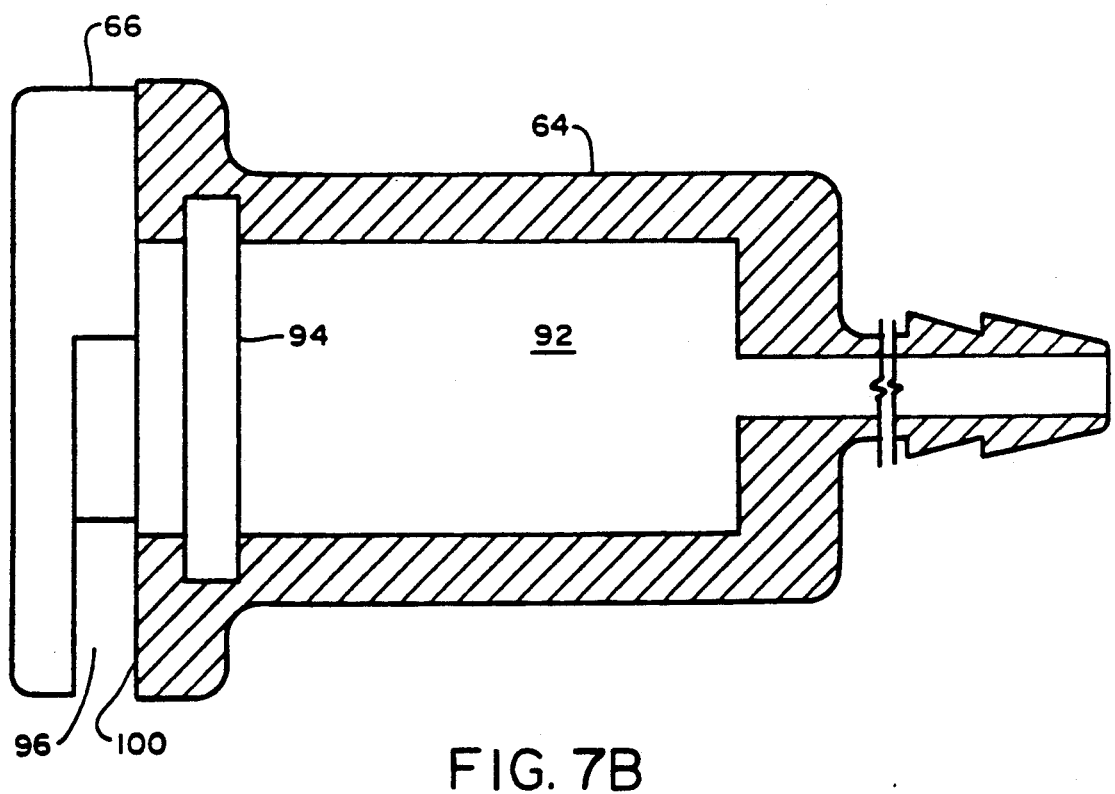

Referring to FIGS. 7A and 7B, there is shown the preferred embodiment of the syringe holder 64 with a bayonet-type lock-in mechanism 66. FIG. 7A shows an end view of the syringe holder looking down the center line, while FIG. 7B shows a section of the syringe holder taken along the section line 7B—7B' in FIG. 7A. As in the case of the syringe holder shown in FIG. 5, the syringe holder has an internal passageway 92 in which is formed a groove 94 in which a flexible, autoclavable O-ring is seated. This O-ring engages the side walls of the portion 76 of the syringe barrel in FIG. 4 to form a pneumatic seal. Essentially the only difference between the syringe holder depicted in FIG. 7A and 7B and the syringe holder shown in FIGS. 5, 6A, and 6B is the lock-in mechanism. This lock-in mechanism 66 is comprised of an annular projecting portion 66 in which are formed a pair of L-shaped grooves 96 and 98, which are best seen in FIG. 4. These grooves engage the two projecting tips of the flange 62. To operate the lock-in mechanism, the portion 76 of the syringe barrel is inserted in the passageway 92 and engaged with the O-rings to form the pneumatic seal. This process pulls the projecting portions of the flange 62 into the L-shaped grooves. When the flange 62 is flush with the wall 100 in FIG. 7B, the syringe 38 is rotated approximately one-eighth of a turn to the right, thereby twisting the flange 62 in the lock-in 66 so as to lock the syringe barrel in place in the syringe holder lock-in mechanism as shown at 68 in FIG. 4.

Figure 8:
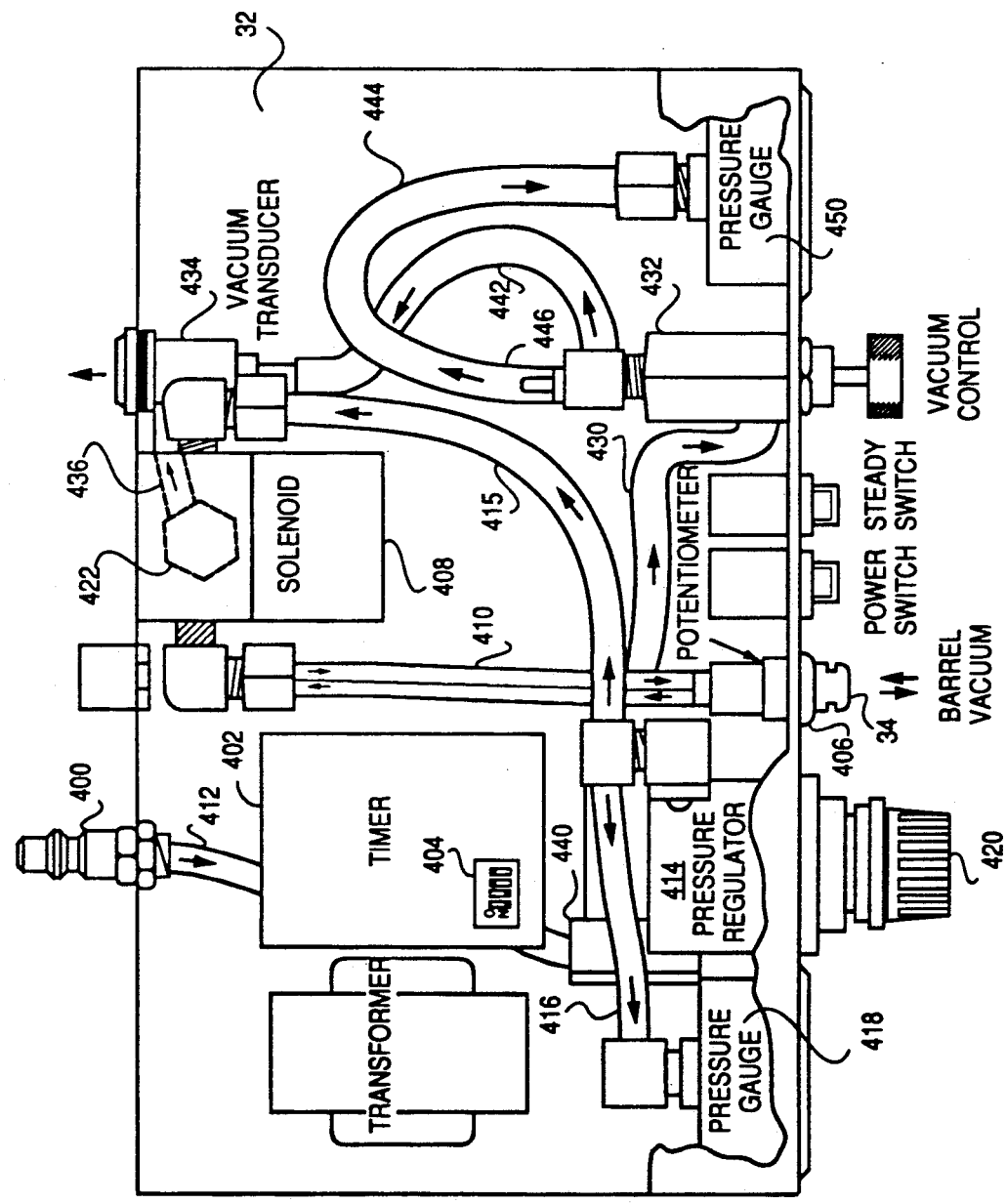
FIG. 8 is a diagram showing the internal structure of the off-the-shelf 1000×L glue injector used as one component of a system according to the teachings of the invention.

Referring to FIG. 8, there is shown the structure of the Model 1000×L glue injector system unit 32 used in one embodiment of the invention. Pressurized gas from an external source, preferably air, enters system unit 32 at port 400. In the "one-shot" mode, the following sequence of events occurs when the footpedal (not shown in FIG. 8, but shown as 52 in FIG. 3) is pressed down. First, upon depression of the footpedal 52, a solid state timer 402 is energized. The timer 402 is EFD part number 2-2006-24PR in this embodiment. A set of four DIP switches 404 are set as shown in FIG. 8 (switches 1 and 2 are off and switches 3 and 4 are on preceeding from left to right). The timer 402 then begins a countdown from a preset count. A LED 406 located on top of the system unit 32 lights to indicate a cycle is active. This LED remains on until the cycle is complete.

The timer 402 energizes a solenoid which controls the output air channel 410. Input pressurized air at approximately 100 psi from input air channel 412 enters a pressure regulator 414. This device outputs regulated pressurized air into channel 415 and channel 426. Channel 416 is coupled to a pressure gauge 418 which provides an indication of the output pressure of the regulator 414 to the user. The output pressure of the pressure regulator 414 is controlled by the user by adjusting a knob 420 on the front panel. The pressure regulator is EFD part number 2-2002-XL.

When the solenoid 408 is energized, vacuum (generated by a vacuum transducer described below) is decoupled from output channel 410. At the same time, the pressurized gas in channel 415 is coupled to the output channel 410. In this embodiment, the solenoid 408 is EFD part number 2-2003-24N. The regulated pressure output gas in channel 410 flows out to the syringe (not shown in FIG. 8, but reference numeral 38 in FIG. 3) via pneumatic output 34 and sterile surgical tubing 34a (shown in FIG. 3). Referring to FIG. 3, this gas pressure pushes the sterile viscous material stored in the syringe out the tip of the needle 24.

Referring again to FIG. 8, at the end of the preset time, the timer 402 shuts off thereby denergizing the solenoid 408. The pressurized gas in the syringe, surgical tubing and the output channel 410 is then exhausted to the atmosphere at exhaust port 422. The duration of the pressurized gas pulse can be varied by manipulation of the front panel timer control 54 in FIG. 8. Simultaneously, the solenoid 408 couples vacuum generated by a vacuum transducer 434 to the output channel 410. Referring again to FIG. 3, this vacuum draws the piston 40 of the syringe 48 in FIG. 3 back toward the pneumatic outlet thereby sucking any remaining viscous material at the tip of the needle that is not supposed to be injected back into the syringe.

Vacuum is created by bleeding pressurized gas from channel 430 through a needle valve 432 and the vacuum transducer 434. The needle valve is EFD part number 2-2176-XL. The vacuum transducer 434 is EFD part number 2-2170LV. The vacuum transducer converts pressurized gas to vacuum in channel 436 which the solenoid 408 couples to output channel 410 at certain times as described above. The pressurized gas channel 430 is coupled by a tee connection 440 to the input pressurized gas channel 412. The needle valve 432 controls the volume flow rate of pressurized gas in a channel 442 to the vacuum transducer 434. A channel 444, coupled by a gauge restrictor 446 to the needle valve, couples the gas pressure in channel 442 to a pressure gauge 450 which provides an indirect indication on the front panel of the system unit 32 of the relative level of vacuum being generated by the vacuum transducer 434.

This completes a "one-shot" pulsed type operation.

Steady state or continuous injection is also possible by switching the steady switch 50 to the steady position. This bypasses the timer 402 and causes the solenoid 408 to be controlled directly by the footpedal 52 in FIG. 3. As long as the footpedal 52 is depressed, the solenoid 408 remains energized to a state where pressurized air from channel 415 is coupled to output channel 410. This provides a steady stream of viscous fluid for injection. When the footpedal is released, vacuum is automatically coupled to the output channel 410 as in the case of the "one-shot" mode.

Figure 9:
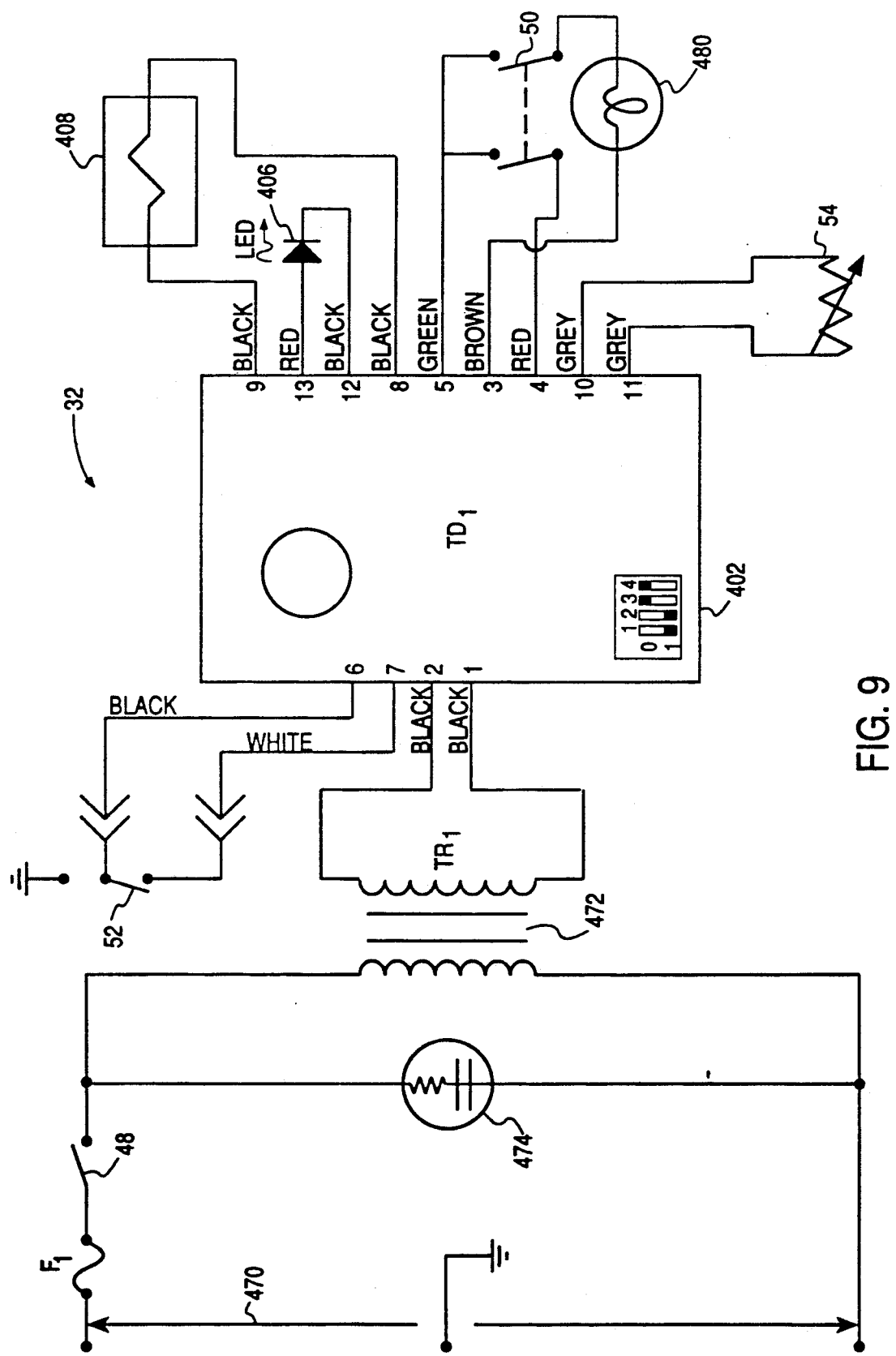
FIG. 9 is an electrical schematic diagram of the off-the-shelf 1000×L glue injector.

Referring to FIG. 9, there is shown a schematic diagram of the internal electrical structure of the EFD Model 1000×L glue injector system unit 32. Input power at 115VAC is applied to input port 470. Fuse F, and on/off switch 48 apply this power to a step down transformer 472 which steps the voltage down to 24 volts. Power on indicator lamp 474 indicates when power is applied to the unit. Footpedal switch 52 is directly coupled to timer 402 as is steady switch 50, time control 54 and solenoid 408. LED 406 lights when solenoid 408 is energized and pressurized air is being applied to the syringe. Lamp 480 lights whenever the steady switch 50 is in a position to place the system unit in steady mode.

Although the invention has been described in terms of the preferred and alternate embodiments disclosed herein, those skilled in the art will appreciate many modifications which may be made without departing from the spirit and scope of the invention. All such modifications are intended to be included within the scope of the claims appended hereto.

What is claimed is:

1. A method of injecting viscous material into an eye between a membrane and a retina using a pneumatic injection unit having a pneumatic output and a pressure control for setting the maximum pneumatic pressure at said pneumatic output comprising the steps of:
   pneumatically coupling a sterile syringe to said pneumatic output, said syringe having a hollow needle and a sharp point and storing a sterile viscous material to be injected;
   applying pneumatic pressure to said syringe and examining the flow rate of said viscous material emerging from said hollow needle;
   adjusting the pneumatic pressure until the flow rate is acceptable;
   placing the tip of said needle at the position in the eye where the viscous material is to be injected;
   applying selected pneumatic pressure until a desired amount of said viscous material has been injected; and
   automatically applying the vacuum to said pneumatic output upon termination of the application of pneumatic pressure to said pneumatic output.

2. A method of injecting viscous material into an eye between a membrane and a retina using a pneumatic unit having pneumatic pressure generation apparatus including a variable pressure control, and a pressure control switch and having a pneumatic output coupled to a syringe having a needle with a sharp point, said syringe storing the material to be injected comprising the steps of:
   (1) setting the desired pneumatic pressure by observing the flow rate of material from the tip of said syringe during a sample injection outside said eye by activating said pressure control switch to apply pneumatic pressure to said output and by manipulating said variable pressure control until the desired flow rate has been achieved;
   (2) setting the desired time interval for a pneumatic pulse at said output generated during a one-shot mode by selecting said one-shot mode by manipulation of a mode select switch and doing a sample injection outside the eye by activating said pressure control switch a plurality of times to generate a plurality of pneumatic pulses at said output and manipulating a variable timer control to adjust the time duration of each pulse until the desired time duration is found;
   (3) selecting either said one-shot mode or a continuous mode by manipulation of said mode select switch;
   (4) if the one-shot mode is selected, placing the needle in the location in the eye where injection is desired and activating said pressure control switch and holding said needle in the desired place until the time duration of the pneumatic pulse has elapsed;
   (5) if the continuous mode is selected, placing the needle of said syringe in any place in the eye where injection of said material is to occur and activating said pressure control switch until a desired amount of material has been injected and then deactivating said pressure control switch;
   (6) automatically applying a vacuum to said pneumatic output upon termination of the application of pneumatic pressure thereto; and
   (7) repeating steps 4, 5 and 6 at any other locations in the eye deemed necessary.

3. The method of claim 2 wherein said pneumatic pressure generation apparatus includes vacuum generation apparatus and a variable vacuum control which applies a selected amount of vacuum to said syringe following the application of pneumatic pressure thereto, wherein the steps of performing sample injections outside the eye include the substeps of manipulating said variable vacuum control until the level of vacuum applied following an injection is sufficient to prevent excessive, undesired injection.

4. A method of injecting viscous material into an eye between a membrane and a retina using a pneumatic unit having pneumatic pressure generation apparatus including a variable pressure control, and a pressure control switch and having a pneumatic output coupled to a syringe having a needle with a sharp point, said syringe storing the material to be injected comprising the steps of:

(1) setting the desired pneumatic pressure by observing the flow rate of material from the tip of said syringe during a sample injection outside said eye by activating said pressure control switch to apply pneumatic pressure to said output and by manipulating said variable pressure control until the desired flow rate has been achieved;

(2) setting the desired time interval for a pneumatic pulse at said output generated during a one-shot mode by selecting said one-shot mode by manipulation of a mode select switch and doing a sample injection outside the eye by activating said pressure control switch a plurality of times to generate a plurality of pneumatic pulses at said output and manipulating a variable timer control to adjust the time duration of each pulse until the desired time duration is found;

(3) selecting either said one-shot mode or a continuous mode by manipulation of said mode select switch;

(4) if the one-shot mode is selected, placing the needle in the location in the eye where injection is desired and activating said pressure control switch and holding said needle in the desired place until the time duration of the pneumatic pulse has elapsed;

(5) if the continuous mode is selected, placing the needle of said syringe in any place in the eye where injection of said material is to occur and activating said pressure control switch until a desired amount of material has been injected and then deactivating said pressure control switch;

(6) automatically applying a vacuum to said pneumatic output upon termination of the application of pneumatic pressure thereto;

(7) repeating steps 4, 5 and 6 at any other locations in the eye deemed necessary; and (8) injecting at a sufficient number of places to separate said membrane from said retina and isolate or break all attachment points between said membrane and said retina followed by working a horizontally oriented intraocular scissors through said viscous material to the point of each attachment not yet broken and severing the attachment followed by aspiration of the membrane and the remaining viscous material from the eye;

wherein said pneumatic pressure generation apparatus includes vacuum generation apparatus and a variable vacuum control which applies a selected amount of vacuum to said syringe following the application of pneumatic pressure thereto; and wherein the steps of performing sample injections outside the eye include the substeps of manipulating said variable vacuum control until the level of vacuum applied following an injection is sufficient to prevent excessive, undesired injection.

5. A method of injecting viscous material into an eye between a membrane and a retina using a pneumatic unit having a variable pressure control, a variable timer control and a pressure control switch and having a pneumatic output coupled to a syringe having a needle with a sharp point, said syringe storing the material to be injected comprising the steps of:

setting the desired pressure by observing the flow rate of material from the tip of the needle of said syringe during a sample injection outside said eye by activating said pressure control switch to apply pneumatic pressure to said output and by manipulating said variable pressure control until the desired flow rate from the tip of said needle has been achieved;

setting the desired time interval for a pneumatic pulse at said output generated upon activation of said pressure control switch and doing a sample injection outside the eye by activating said pressure control switch a plurality of times to generate a plurality of pneumatic pulses at said output and manipulating said variable timer control to adjust the time duration of each pulse until the desired time duration is found;

placing the tip of the needle at the location in the eye where the injection is to be made and activating said pressure control switch such that a pulse of pneumatic pressure having selected, programmable characteristics is applied to said syringe thereby forcing a predetermined amount of said material from the tip of said needle; and repeating the step next above at a plurality of other locations if necessary.

6. A method of injecting viscous material into an eye between a membrane and a retina using a pneumatic unit having a variable pressure control, a variable timer control and a pressure control switch and having a pneumatic output coupled to a syringe having a needle with a sharp point, said syringe storing the material to be injected comprising the steps of:

setting the desired pressure by observing the flow rate of material from the tip of the needle of said syringe during a sample injection outside said eye by activating said pressure control switch to apply pneumatic pressure to said output and by manipulating said variable pressure control until the desired flow rate from the tip of said needle has been achieved;

setting the desired time interval for a pneumatic pulse at said output generated upon activation of said pressure control switch and doing a sample injection outside the eye by activating said pressure control switch a plurality of times to generate a plurality of pneumatic pulses at said output and manipulating said variable timer control to adjust the time duration of each pulse until the desired time duration is found;

placing the tip of the needle at the location in the eye where the injection is to be made and activating said pressure control switch such that a pulse of pneumatic pressure having selected, programmable characteristics is applied to said syringe thereby forcing a predetermined amount of said material from the tip of said needle;

repeating the step next above at a plurality of other locations if necessary; and injecting at a sufficient number of places to separate said membrane from said retina and isolate or break all attachment points between said membrane and said retina followed by working a horizontally oriented intraocular scissors through said viscous material to the point of each attachment not yet broken and severing the attachment followed by aspiration of the membrane and the remaining viscous material from the eye.

7. A method of injecting viscous material into an eye between a membrane and a retina using a pneumatic unit having a variable pressure control, a variable timer control, and a pressure control switch and having a pneumatic output coupled to a syringe having a needle with a sharp point, said syringe storing the material to be injected, comprising the steps of:

- setting the desired pneumatic pressure by observing the flow rate of material from the tip of the syringe during a sample injection outside said eye by activating said pressure control switch to apply pneumatic pressure to said output and by manipulating said variable pressure control until the desired flow rate has been achieved;
- setting a desired time interval for a pneumatic pulse at said output by performing a sample injection outside the eye by activating said pressure control switch a plurality of times to generate a plurality of pneumatic pulses at said output and manipulating said variable timer control to adjust the time duration of each pneumatic pulse until the desired time interval is found;
- placing the tip of the needle at the location in the eye where the injection is to be made and activating said pressure control switch to inject a portion of said viscous fluid at the desired location;
- applying a vacuum to said output automatically upon termination of said pneumatic pulse; and
- repeating the injecting and vacuum application steps at any other desired location in the eye.

* * * * *

UNITED STATES PATENT AND TRADEMARK OFFICE
CERTIFICATE OF CORRECTION

PATENT NO. : 5,120,307
DATED : June 9, 1992
INVENTOR(S) : Wang

It is certified that error appears in the above-identified patent and that said Letters Patent is hereby corrected as shown below:

On title page, and col. 1, line 3, the title should read --METHOD FOR INJECTING VISCOUS FLUID INTO THE EYE TO LIFT RETINAL MEMBRANE--

Col. 3, line 11, delete "1000 X L" substitute therefore --1000XL--

Col. 5, line 5, delete "1000 X L" substitute therefore --1000XL--

Col. 5, line 9, delete "1000 X L" substitue therefore --1000XL--

Col. 5, line 60, delete "selfadhering" substitute therefore

--self-adhering--

Col. 6, line 48, delete "1000 X L" substitute therefore --1000 X L--

Col. 10, line 20, delete "1000 X L" substitute therefore --1000XL--

Col. 11, line 35, delete "1000 X L" substitute therefore --1000XL--

Signed and Sealed this

Fifth Day of October, 1993

Attest:

BRUCE LEHMAN

*Attesting Officer*    *Commissioner of Patents and Trademarks*